United States Patent [19]
McGuire

[11] 3,978,470
[45] Aug. 31, 1976

[54] MULTI-CHANNEL DATA COLOR DISPLAY APPARATUS

[75] Inventor: Lawrence T. McGuire, Wauwatosa, Wis.

[73] Assignee: Midwest Analog and Digital, Inc., Wauwatosa, Wis.

[22] Filed: July 10, 1974

[21] Appl. No.: 487,010

[52] U.S. Cl. .............................. 340/324 AD; 315/30
[51] Int. Cl.² ............................................. G06F 3/14
[58] Field of Search .................. 340/324 A, 324 AD

[56] References Cited
UNITED STATES PATENTS

| | | | |
|---|---|---|---|
| 3,248,650 | 4/1966 | Bialkowski et al. | 324/121 |
| 3,406,387 | 10/1968 | Werme | 340/324 A |
| 3,469,252 | 9/1969 | Bet | 340/324 A |
| 3,474,438 | 10/1969 | Lauher | 340/324 A |
| 3,577,031 | 5/1971 | Welsh et al. | 315/13 |
| 3,585,440 | 6/1971 | Lee et al. | 340/324 A |
| 3,652,999 | 3/1972 | Hjort et al. | 340/324 A |
| 3,686,662 | 8/1972 | Blixt et al. | 340/324 A |
| 3,765,009 | 10/1973 | Graves et al. | 340/324 A |

*Primary Examiner*—David L. Trafton
*Attorney, Agent, or Firm*—Andrus, Sceales, Starke & Sawall

[57] ABSTRACT

A multi-channel display apparatus includes a computer having a random access memory means for storing of the continuous monitored data and for driving of a multiple-channel television unit, with each channel identified by a preselected unique color. Vertical scan lines generate line display segments in each channel. The computer stores line segment definition information which is compared with a beam driver control to activate one color driver which is preset to produce a predetermined color presentation for the channel. Alphanumeric data may be displayed in selected channels through a separate character channel having a character generator with an internal sequence system to read-out the selected character and channel location, with an auxiliary decoder selecting the color driver. A computer processor and a display controller are operated through an interlocking control, with the controller monitoring the computer and allowing computer-memory coupling. During a character display, the computer kills the processing cycle, while during a graphical display, the line segment generation is interrupted at an appropriate time and held in standby. The processing system for line segment display includes buffer and latch registers for each line in each channel. A digital logic comparator driven from a single coordinate count unit, reset at the beginning of each scan line, sequentially reads the register and activates channel related color drivers. A synchronizing signal unit provides horizontal and vertical sync signals for driving of the television unit and processor and the sync clock is coupled to drive the comparator. Each driver includes continuously variable primary color signals which are connected to the television set by suitable mixer to permit preset of each channel to any desired color. The channels can be located on the display screen in separate or superimposed locations and related graphical and character channels can be displayed in corresponding color by suitable logic circuitry.

28 Claims, 2 Drawing Figures

MULTI-CHANNEL DATA COLOR DISPLAY APPARATUS

BACKGROUND OF THE INVENTION

The present invention relates to a multi-channel color display apparatus and particularly to such an apparatus for displaying of different monitored data in channels with individual unique color per channel.

In the monitoring of various functions and processes, it is often desirable to produce a continuous, visual presentation related thereto. For example, in the monitoring of human body functions and the like, such as cardiac conditions, it may be desired to produce an automatic display of various interrelated medical data. A continuous display of the patient's ECG trace, blood pressure, temperature and the like, must be, under conditions, monitored on a continuous basis. In manufacturing systems, environmental controls and the like, visual display is often desired. Various systems have been suggested for providing visual display of such monitored information at a remote location. Generally, the various prior art systems have suggested the concept of transmitting of the information to a storage oscilloscope device or the like with scanning means to scan and transmit the signals to various viewing stations, or to one or more viewing stations, through a selective scanning concept. Generally such devices have employed black and white video presentations although color presentations have been suggested, for example, as shown in U.S. Pat. No. 3,642,634. Generally, where the color concept is employed, each point or individual scan line has been individually color coded to control the related trace. Although such devices provide a means of very satisfactory display concepts, they are generally relatively complicated, expensive and, therefore, of somewhat limited application. More recently, data has been transmitted and stored in shift registers with the information sequentially transferred to a display unit, for example, as shown in U.S. Pat. No. 3,745,407.

SUMMARY OF THE PRESENT INVENTION

The present invention is particularly directed to a multi-channel data display color display apparatus including a computer having a random access memory means for storing of the continuous monitored data and for driving of a multiple channel display means, with each channel identified by a selected unique color. The present invention particularly in one unique aspect uses a conventional commercial television receiver reoriented to present vertical scan lines and appropriate beam controls to generate line display segments in each channel and thereby generate a total display of the monitored data. The output of the random access memory means is cyclically and repetitively transmitted in time-spaced relation through a color display control for separating of the signals for display in related display channels and coupling them to a common color driver means. In accordance with the present invention, the computer stores the defintion of line segment for each scan line in a storage means and the information is compared with a beam driver control to activate the color driver means accordingly. The color driver means is preset to produce a predetermined color presentation in each channel and thereby provide a color-coded presentation. The position of each channel can be controlled to produce separate or superimposed graphical displays with the color distinction between the channels. The display apparatus may, in accordance with another aspect of this invention, also include means to display alphanumeric data in selected channels. In this aspect of the invention, a character memory bank is provided having means to output to a character generator having an internal sequence system to readout the selected character and channel location with an auxiliary decoder to select the color and channel identification. The present invention provides a system which can employ the various standard presentation techniques associated with commercial television such as split screen presentation with alphanumeric information. The combined computer-display system with a time shared memory provides for programmed version and storage of the monitored information with the necessary versatility in use and processing of the information. Thus, the sampling of information is essentially independent of the output processing and display. The medical or any other monitored data is sampled at any desired reasonable rate and stored in computer memory which establishes a record of the channel and the display line. The computer processing means and the display means are operated through an interlocking control, with the computer establishing the overriding control of the transfer of information to and from memory. A horizontal and vertical sync signal generator drives the television display means to cyclically transfer the data from memory into an auxiliary processing system for display. The computer, however, may terminate the operation of the processing system at any time and establish access to the memory bank for processing. During a character display, the computer kills the processing cycle, while during a graphical display, the computer request is anticipated and the line segment generated interrupted at an appropriate time.

The processing system for graphical display includes data information buffer and latch registers for each line in each channel to be displayed. At the end of the scan of the previous line, the latch registers are outputed or transferred to a corresponding pair of control or latch registers. The output of the control or latch registers are coupled as the inputs to a pair of digital logic comparing units driven from a single coordinate count unit, which is reset at the beginning of each scan line.

The present invention employs the conventional television receiver and interlaced scanning is employed for the graphical display. The sequential entry of information into the several pairs of buffer registers and transfer to the control registers is controlled by the output signals of the television receiver synchronizing signal unit and particularly the horizontal and vertical sync signals and the odd and even frame signals. The coordinate count unit is driven from the sync clock and is reset at the beginning of each scan line.

The digital stored memory signals in the registers are compared with a counter and when a selected comparison with the first register exists the color gun units are driven to illuminate a correspondingly positioned display coordinate of the conventional television set and illumination is maintained until a selected comparison with the second register exists. In this manner, the unit continuously controls the individual coordinates of the respective traces illuminating or presenting a coordinate when in a proper time position in accordance with the data.

The character display processing system includes a suitable readout with its own internal sequence to produce predetermined characters in response to a coded binary input, with the output coupled through a channel decoder.

The color interfacing includes individual preset channels for properly shaping and transmitting of the channel control signals, with the output being interrelated to a suitable position and condition control interlock. The channel output may generate three-gun control signals of a predetermined relationship and thereby establish a predetermined color signal uniquely related to that particular channel. The television sync signals are derived from the same sync signal generator or source as the timing signals for the transfer or interface with the memory unit such that the coordinate signal is predetermined and merely the assignment of its position for the related channel is controlled by the signal processing. Thus the processing of the information for each coordinate is minimized while maintaining the highly desirable color separation control.

The channels can be located on the display screen in separate or superimposed locations and related graphical and character channels can be displayed in corresponding colors by suitable logic circuitry.

Further, to ensure a continuous appearing color graph, the initial coordinate is emphasized by generating of a pulse signal in response to each channel signal. The pulse signal is applied to the color driver circuits in synchronism with the initial turn-on of the channel.

An alarm control can be incorporated into the system to change from one color to a different color under certain alarm or preset conditions.

Thus, the present invention provides a highly simplified basic concept in producing of a preset color channel with means for sequentially coupling of the data to the color drivers of an associated channel at an appropriate time to produce the multi-channel display on a conventional television unit or the like. The present invention provides a relatively simple reliable means of collecting and visually displaying various interrelated or separate data on a single drive or display unit in a relatively simple and inexpensive construction.

BRIEF DESCRIPTION OF DRAWING

The drawing furnished herewith illustrates the best mode presently contemplated by the inventors for carrying out the subject invention in which the above advantages and features are clearly disclosed as well as others which will be readily understood from the following description of the embodiments shown.

In the drawing.

DESCRIPTION OF THE ILLUSTRATED EMBODIMENTS

Figure 1:
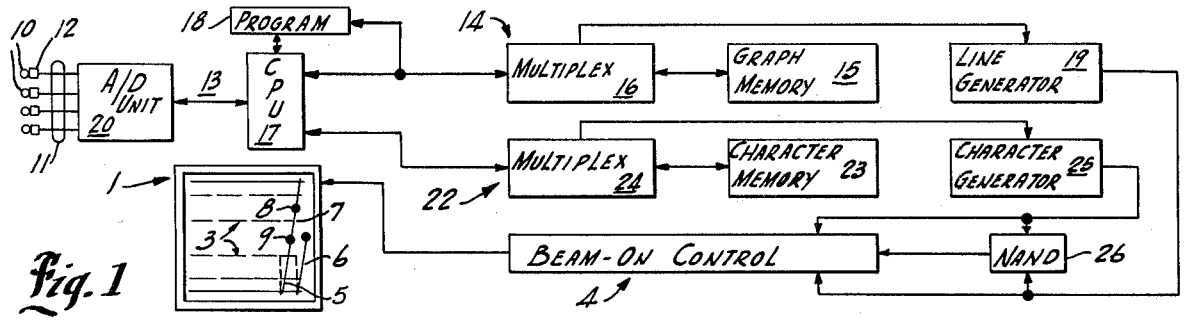
FIG. 1 is a block diagram of a display system constructed in accordance with the teaching of the present invention for graphical and alphanumeric information.

Referring to the drawing and in particular to FIG. 1, the present invention is especially constructed to employ a conventional color television set 1 as a display means and the set 1 is diagrammatically illustrated for display of monitored information on a tube or screen 2 such as industrial processes or controls, operating apparatus data, physiological data of a patient or the like. The present invention involves the simultaneous presentation of a plurality of different types of information in graphical form on display portions or channels, shown diagrammatically by four channel lines 3 on the display means 2. The tube 2 is driven from a beam-on control 4 which is wired to establish individual colors for each of the several channels 3. Although shown as individual vertically spaced channels 3, color is employed as the basically distinguishing feature and the channels may be superimposed or displaced in any desired manner within the present invention.

Further, in accordance with the teaching of the present invention, the television beam is interlaced with the conventional odd and even scan lines 5 and 6 driven through the conventional suitable synchronizing control. A small expanded portion of line 5 is shown and only the starting portion of line 6 for simplicity of illustration. The display means 2 is reoriented by 90° from the conventional position such that the horizontal scan lines 5 and 6, in fact, are vertically oriented, as shown in FIG. 1. The plurality of distinct graphical display channels 3 are generated by forming of line segments 7 shown as heavy portions on scan lines 5 and 6 with only the starting coordinate 8 and the final point or coordinate 9 determined, with the beam being held on therebetween. For example, the invention may be applied to the monitoring of a plurality of body functions of a patient, such as those related to the cardiac condition of a patient. Suitable pick-up means shown as sensing electrodes 10 may be attached to a patient for detecting various body functions such as the conventional ECG trace, temperature, pressures and other related functions or characteristics which are preferably monitored on a continuous basis. The output signal leads 11 are operably connected to suitable transducer means 12 which will convert the sensed signals into predetermined analog voltage signals or the like. The several analog signals are coupled through a special computer means 13 which is coupled to the television set 1 through an interlocking and interfacing means 14 to drive and produce a visual presentation of the information on a particular interrelated channel 4.

Generally, in accordance with the present invention, the data from the several electrodes 10 or other suitable pick-ups, are sequentially sampled and stored in a shared random access memory 15 via a multiplexer 16 under the control of a computer processing unit 17 and computer program unit 18 of the computer means 13. The stored data is sequentially updated and fed to control the television beam-on control 4 by suitable operation of a processing unit 19 coupled by multiplexer 16 to the memory 15 for time spaced and computer controlled operation.

The computer means 13 may be a small digital minicomputer for sampling, storing and processing of the sampled data. A multiple channel analog-to-digital converter 20 is connected to the respective input transducers 12 and produces corresponding digital data outputs to the computer processing unit 17 under control of the program unit 18.

Although shown with only four channels, a greater number will normally be used. In a practical construction an eight channel unit has been made and it may be readily expanded to 32 channels by provision of an appropriate sized memory. The digital computer is automatically programmed by the program unit 18 to continuously and sequentially sample the data and to store such data in its shared memory 15, automatically keeping track of the particular channel 3 and the horizontal line interlacing. The multiplexer 16 is coupled to the interfacing processing unit 19 which includes a sequence controller operated in synchronism with the scan lines 5 and 6 to sequentially load the graphical data for each line segment 7 and having an output which sequentially activates the beam-on control 4 to generate the line segments 7 with a predetermined color for each channel.

A second similar processing channel or system 22 is provided for producing selected alphanumerica display on preselected channels 3. The system 22 generally includes a separate character shared memory bank 23 coupled to the computer processing unit 17 via a multiplexer 24. A character generator 25 is also coupled by the multiplexer to the shared memory banks 23. The output of the generator 25 is coupled to drive the beam-on control 4 to develop the particular programmed characters with predetermined color for each channel.

Further, as shown in FIG. 1, the outputs of the graphical display channels 14 and the alphanumeric channels 22 may be ANDED by a logic unit 26 to provide an output to the beam-on control 4 with the selected channels of the same color.

In operation, the computer processor unit 17 continuously updates and processes the data with controlled entry thereof into the memory banks 15 and 23. As more fully developed hereinafter, the processing channels or systems 19 and 25 are normally coupled to the memory banks 15 and 23 to continuously and in proper sequence through internal sequence control means activate control 4 during each scan line 5 and each scan line 6 to generate related graphical information and alphanumeric information in visual display. Each channel 3 is color coded to permit distinguishing between the several channels.

Figure 2:
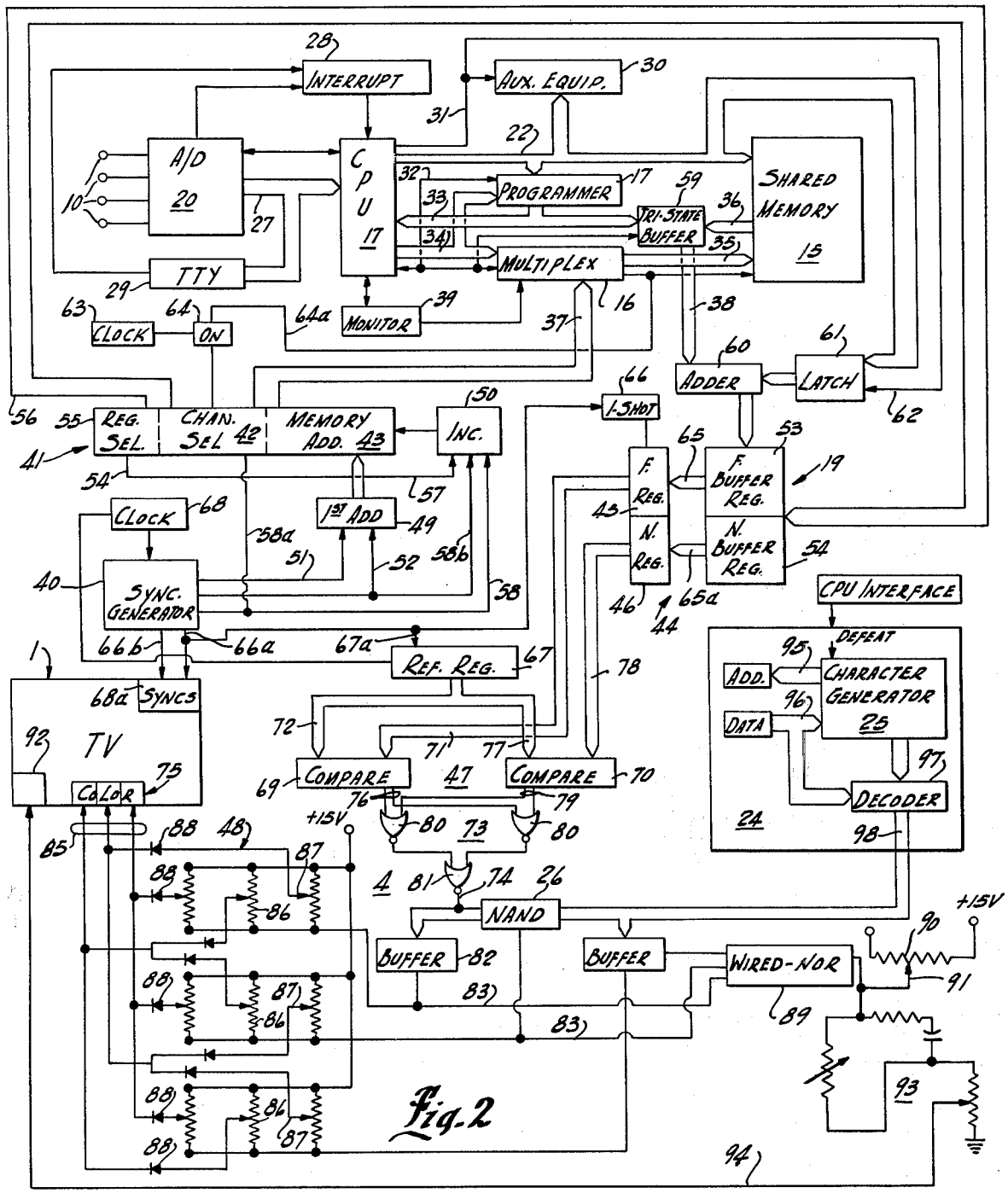
FIG. 2 is a detailed block diagram of the system of FIG. 1 and illustrating the separate processing systems for the graphical display and the alphanumeric information.

In FIG. 2, a detailed block diagram illustrates a preferred apparatus for implementing the color coded multiple-channel display in accordance with the teaching of this invention, with a detailed illustration and description given for the graphical display channel 14. The character generator channel 22 is briefly discussed and references to channel 14 for a complete understanding of the system.

Referring particularly to FIG. 2, the computer processing unit 17 is connected via a data input bus 27 to sample the data from the A/D converter 20 on a time basis and to transmit the converted information via a data output buss 22 to memory 15 for storage. The usual computer interrupt unit 28 is provided to provide the control logic and to signal the processing unit 17 for coupling of the A/D converter 20 and detecting termination of the cycle. A teletypewriter 29 may also be coupled to the computer unit 17 for communication under the control of the interrupt unit 28. Bus 22 is also connected to the program unit 17 to provide the necessary information interchange, as well as to a peripheral data processor 23, such, for example, as a video character generator which is, of course, controlled from the processing unit 17 in accordance with a conventional control, as shown by signal lines 31 and 32.

The information relative to the position of the lines and channels of display means 2 is coupled between the processor 19 and the program unit 17 via a memory data input bus 33 and a memory address bus 34. The several memory buses 33 and 34 are also coupled by the multiplexer 16 to corresponding shared memory address buses 35 and shared memory information data bus 36 of the memory unit 15 and to the graphic address bus 37 and graphic data bus 34 of the interfacing processing unit 19.

The computer processing unit 17 is adapted to provide an overriding control to obtain communication with the shared memory at will. An interlocking status monitor control unit 39 is interconnected to signal the unit 17 and anticipates the demand of the computer 13 to produce a signal to multiplexer 16 of that demand. The multiplexer 16 then signals the graphical display interface 19 to hold momentarily until the computer has completed the communication or fetch cycle.

The interface unit 19 is normally activated and is controlled by the output of a television sync signal driver or generating unit 40, as hereinafter described, to transmit the shared memory data to the display processing system via bus 36 and 38 in response to input address information via buses 37 and 35.

The memory storage unit 15 provides the data for each channel 3 and the processing unit 19 includes separate signal processing channels with selected common sequencing elements. Each of the channels is similarly constructed to drive the beam-on control to properly illuminate the line segment 7 on the screen and correspondingly generate a preselected color trace in accordance with the sampled data. Because each of the signal channels is similarly constructed, a single one of the channels is shown and described in detail.

The interfacing system 19 of the shared memory 15 to the display means 1 is controlled by a sequence controller means 41 which selectively and sequentially establishes the transfer of the information on a line by line basis.

Generally, the sequence controller includes a channel selector 42 and addressing memory 43 to select the channels in a repetitive manner, and to effect transfer of the data from memory 15 to an appropriate storage stage 44, which includes a pair of storage registers 45 and 46 for each channel and which receives and stores the starting and stopping coordinates for each line segment 7. A comparing or reading stage 7 sequentially reads the stored information and activates a three gun color driver stage 48 to produce the preselected color display for the channel read. The television sync signal driver or generator 40 is included to generate the necessary synchronizing signals for the several stages 42, 43, 47 and 48 and establish the proper timing of the data transfer and the processing with the generation of scan lines 5 and 6.

The character display system 24 is not a single function system and does not employ the line segment 7 type of display. The character system 24 employs a separate character generator 25 which receives the character information and through a separate internal sequence generates the driving signals for turn-on and turn-off of the beam. The system may employ a sequence control similar to that of the graphical display, as hereinafter described.

More particularly, the address memory bank 43 is diagrammatically illustrated including a first address selector 49 and an address increment or stepping unit 50. The first address selector 49 is illustrated as a preset, hardwired input to the address memory bank 43 and is coupled to the television sync driver 40 by an odd-line sync signal line 51 and an even-line sync signal line 52 to initiate each display scan of the screen from a preselected starting address. The first address unit 49 may, of course, be a presettable, latch unit driven from the computer for further automatic movement of the display across the screen, positioning on the screen and the like.

More particularly, in the illustrated embodiment of the invention, the pair of control registers 45 and 46 for storing of the data identifying the beginning point 8 and the terminal point 9, respectively, for a line segment 7 is withdrawn from the shared memory 15 via bus 38 and placed in a pair of related buffer registers 53 and 54, shown and identified as "F" and "N" registers for the purpose of clearly relating to the subsequent description. The buffer registers 53 and 54 are loaded during a scan line drive under the control of the sequence controller 41. The coordination and synchronism between the display and the memory is controlled by providing channel and register selection output synchronism in response to signals from the television synchronizing signal generator 33. Thus, the sequence controller 41 includes the channel load counter 42 connected to a register select unit 55, the output of which is coupled by a bus 56 to sequentially activate the buffer registers 53 and 54 during the loading cycle to temporarily store the data for subsequent transfer to the processing registers 45 and 46. The channel selector 42 sequentially activates the F registers 53 to insert each "0" address. The F/N register select unit 55 is then toggled with the output connected by line 57 to activate the address increment driver to the next or "1" address in memory 43. The channel selector recycles and loads all the N registers 54.

The address increment unit 50 is thus driven to sequence the address memory for each scan line 5 and 6 for transfer of data in proper sequence to the registers 45 and 46, from the even frame output of the register selector 53 via line 54 to properly switch from the one set of buffer registers 45 to the second set of N buffer registers during the loading thereof from the shared memory. The increment unit 50 is enabled from channel select sync signal line 58 which also is connected by line 58a to activate or cycle the channel selector 42. The increment address unit 50 is further driven from an odd frame sync signal line 58b tapped to line 52 to properly step the address at the beginning of each odd line scan.

The channel load counter 42 provides sequential channel selections with the memory address 43 transmitted via a cable 37 to the multiplexer 16. The memory is thus addressed via bus 35 and the related data is transferred from memory via the graphical data output bus 36 to a tri-state buffer 59 of the multiplexer 16. The tri-state buffer 59 is a well-known device and is connected to directly transmit the data to the F and N buffer registers 53 and 54 through an 8 or 9 bit adder 60 which is selectively set by a latch unit 61 coupled to the computer processing bus data bus line 22 and controlled by a control line 62 from the computer processing unit.

The adder 60 is employed to provide a split screen presentation on the screen. Thus, the adder is a conventional logic element which, when activated, proportionately converts all the data information by a given percentage and shifts the presentation to the upper or lower half of the screen.

The channel selection counter 42 thus sequentially counts or steps from channel 0 through channel 3 with the initial address for each channel. The selection toggle unit 55 is activated by the termination of the first channel selection sequence to select the alternate or N register buffers 54, and simultaneously to toggle the address bank 50 to read the next address.

The channel selector 42 is driven from a clock 63 which is coupled thereto through a suitable on-off control gate 64. The normal state of the gate 64 is to transmit the clock pulse and thereby sequence the channel selector 42 whenever the latter has been enabled. The gate 64 has a stop-input connected by a defeat line 64a to an output of the multiplexer 16 which activates the shared memory for communication with the computer processing unit 17.

As previously discussed, the computer means 13 has priority and can couple the memory banks 15 and 23 at any time. The character generator unit 25 is directly disabled or defeated any time with the particular display points blanked. This is acceptable as the character information is only presented every second or so and will not create any adverse flickering.

The graphical display is synchronized and the addressing and channels are held in step with the display means, and the processing is desirably interrupted at the end of a line readout.

In the illustrated embodiment, the monitor 39 anticipates the computer demand for memory and holds the processing system 41 inactivated at the end of a line readout cycle for a selected period which is sufficiently great to permit the computer fetch cycle, after which the processing system is again released and will proceed with the next line. Thus the computer time requirement is always sufficiently short, and the anticipatory time is sufficiently great to permit the desired sequencing with the display means momentarily held in an interrupted state. The computer will complete a "fetch" or communication readily within the line retrace time of the beam. Registers 45 and 46 are coupled to registers 53 and 54 via buses 65 and 65a and the data or information is simultaneously transferred for all graphical display channels 3 at the end of each scan line 5 or 6.

In the illustrated embodiment a "one-shot" circuit unit 66 of any suitable construction is connected to the blanking signal output line 66a of the television sync generator unit 40 and activates the registers 45 and 46 to setting of registers 53 and 54.

The actual information transfer to the beam-on control 4 is controlled by detecting the digital output of register 45 to turn-on the scanning beam and detecting the output of register 46 to turn-off the beam and thereby generate one line segment 7. After the outputs of the several registers 45 and 46 for each channel have been sequentially detected and have activated the beam, all the line segments 7 of one scan line 5 are completed. The registers 45 and 46 are then updated for the next scan line 5 during the blanks and retrace time and the cycle is repeated. During each line generating cycle, the buffer registers 53 and 54 are updated.

More particularly, the setting of the registers 45 and 46, and therefore the point to turn-on and turn-off of the display beam, is determined by driving of a counter 67 to the setting of the registers 45 and 46. Thus the counter 67 is any suitable digital output counter and in the illustrated embodiment of the invention is shown driven from the television synchronizing circuit clock 68.

The signal generator 40 is driven from a suitable clock 68 with a vertical sync and blank signal lines 66a and 66b connected to the television sync circuit 68a. The generator 40 further develops the various keying signals at the lines 51, 52 and 58 for operating of the interfacing means to load the registers 53 and 54 in proper sequence.

The counter 67 is reset at the beginning of each scanning line, for example, as a result of the horizontal blanking signal appearing at line 66a and shown by the connecting input reset line. The output of the counter 67 and the outputs of registers 45 and 46 are compared in a continuous manner through related digital signal comparators 69 and 70. Thus the comparator 69 includes a first input connected via a bus 71 to the output of the registers 45. A second input is connected via a bus 72 to the output of the counter 67. The output of the comparators 69 and 70 are combined in a separate logic unit 73 for each pair of registers and thus for each individual channel 3 and forms a control signal line 74 to one of a plurality of color level control units 48 to activate three color gun drivers 75 for producing the selected color for that channel. Thus, at the very initial start of a scan line 5, the counter 67 is reset. Consequently, its input is at reference or zero level. The related output of register 45 creates a beam-off signal from comparator 69 to logic unit 73 via a channel bus 76 and the beam is held off or deenergized. The counter 67 begins to count in synchronism with the movement of the scan line 5. When the count of the counter 67 equals the setting of the register 45 the comparator 69 will detect the coincidence and provide a beam-on signal via line 74. Further, for each particular channel the level controls are uniquely related to produce a predetermined color for the line segment 7. Thus the corresponding line segment 7 is generated and continues until the comparator 70 produces a turn-off of the beam. The turn-off point 9 is set by the output of the comparator 70 which has one input connected to the output of counter 67 by a bus 77 and the second input connected via a bus 78 to the registers 46. An output bus 79 is connected to the logic unit 73 and when the comparator 70 registers coincidence, the beam unit 48 turns off or deenergizes the beam.

More particularly, the logic unit 73 is shown for one channel and includes a pair of two input NOR gates 80 each having a pair of inputs connected one each to each of the comparators 69 and 70. The outputs of the NOR gates 80 are connected to a third NOR gate 81, the output of which is connected to the channel driver line 74. The first comparison creates an enable signal on channel driver line 74 which is coupled through a suitable buffer inverter unit 82 for that channel. The other channels are driven from separate comparator outputs which are combined by similar logic units to develop control signals on related channel driver lines 74, not shown.

Thus, illustrated line 74 may be coupled through the buffer 82 to a selected color control input line 83 or through the NAND gate 26 to a different color control input line 84.

Thus, the color control unit 48 includes a plurality of individual stages, each of which is similarly constructed to produce three output signals coupled one to each of three input lines 85 to the color gun driver 75. Each stage is similarly constructed and one is described. The stage includes three individual potentiometers 86 having individually adjustable output taps 87. The setting of the taps 87 determines the output voltage and, therefore, the percentage of the color combined with the other two similarly set colors. The taps 87 are connected to the drivers by suitable diode means 88 or other suitable means to isolate the several signals. By providing of a continuous or infinite type control such as produced by a potentiometer of the three primary colors, a corresponding continuous range of colors are obtained for each of the channels.

Thus, the wiring of each channel driver line 74 to a particular color control input line 83 sets one stage of the unit 48 and presets the color for that channel. In FIG. 2, the cable input illustration to buffer 82 and NAND gate 26 indicates the multiple line connections with each channel driver line 74 connected to only one of the input lines.

The apparatus is preferably constructed with the color control taps 87 coupled to exposed adjustment elements for adjustment of the channel colors as desired.

Further, by employing suitable automatic color signal adjustment means, the channel color may be programmed, remotely controlled or the like.

In development of the line segments 7, the initial turn-on will not with the conventional colored television normally be with full intensity. Thus, a slight delay is generally encountered while the intensity of the beam builds to the level set by the color driver stages 48. In the illustrated embodiment, an auxiliary momentary drive-on signal is applied to the intensity control of the television set to emphasize the starting point and thereby develop a continuous, even line intensity.

Thus, in the illustrated embodiment, a NAND-NOR logic unit 89 is connected to all of the color stage input lines 83. The output of unit 89 is connected through a pull-up variable resistor 90 to a positive voltage supply. The tap 91 of the resistor 90 is connected directly to a base line unit 92 of the television set 1 via a wave shaping capacitor-resistor circuit 93. The output of the circuit 93 is connected via the lead 94 to the unit of the television set 1 to increase the intensity during the initial turn-on.

The wave shaping circuit may, of course, be employed to also control the terminal point of the line segment for optimum visual graphical illustration. For example, the wave shaping may thus be selected to produce a slow start and gradual termination to develop a smooth, visual pleasing line graph in each of the graphical display channels. Further, a suitable circuit means may be introduced in any part of the output circuit, for example, in the individual color driver circuits.

The character generating channel, as previously noted, is constructed with the character generator 25 which includes the necessary sequencing to generate selected alphanumeric characters. The generator 25 includes an addressing bus 95 coupled to the shared memory 23 by multiplexer 24 and includes a character select input bus 96 forming a part of the data input from memory. A decoder 97 couples the output of the character generator 25 to the several drivers through an output channel bus 98. The decoder 97 is coupled to bus 96 and receives simultaneous color channel encoded data which selects the channel driver line of bus 98 in accordance with the memory data to receive the character. Thus, the memory unit 23 includes the necessary encoded information as to the particular character to be displayed, the channel and channel location, with the decoder function to apply the character to the appropriate channel color wire or line of bus 96. This is in contrast to the graphical display where the controller provides sequencing of the several channel outputs.

As previously noted, the character channel is otherwise similarly interfaced with the computer means. As the character generator is operating at a very rapid cycle, the generator 25 is defeated or blanked upon receipt of a signal that the computer is about to establish correspondence with the memory unit. Thus, the high speed of the character generator makes a system to hold the unit in a standby mode while the computer is coupled to the memory impractical.

Further, the present invention may, of course, be expanded to provide any number of channels with the time capability of the system, and may be further expanded by employing duplicate display and sequence controller means coupled to the one memory.

Various modes of carrying out the invention are contemplated as being within the scope of the following claims, particularly pointing out and distinctly claiming the subject matter which is regarded as the invention.

I claim:

1. A multiple channel data display apparatus for individual display of a plurality of monitored data as separate single line function graphs on a separate data channel, comprising a computer means having input means to receive the data and processing means for analyzing the monitored data and storing such data in a graphical memory means in accordance with a segment of the related single, line function, a color display means having a variable driver means, one driver means for each of said channels, said display means being connected to said memory means and including a controller means for sequentially withdrawing of said information and applying said information to said individual color driver means to actuate the color drivers in accordance with the line segment data of the related channel, whereby said multiple channels are displayed with preset identifying color for each of said channels.

2. The apparatus of claim 1 wherein each of said plurality of color driver means includes adjustment means for adjusting the color related presentation established for said channel.

3. In the data display apparatus of claim 1, said computer processing means selectively monitors the data and transmits the data to the memory means, said display means having means responsive to said processing means to hold the display means in standby with the computer means communicating with the memory means and thereafter releasing the display means.

4. The apparatus of claim 1 including a multiplexer means coupled between the computer processing means and the graphical memory means, said multiplexer means having an output coupled to the display means and said controller means including inhibit means responsive to a computer demand signal decoupling the shared memory means from the display means and coupling the shared memory means to the computer processing means, said computer means generating an anticipatory signal prior to the actual demand time whereby said controller means completes a line segment and then holds till the terminal end of the computer-memory cycle.

5. The apparatus of claim 1 wherein said graphical shared memory includes data identifying the initiating and terminal points in each line segment for each channel, register means for storing of such point data, said controller means including a sequence means including a channel select means and a memory address means coupled to the memory means to activate transfer of data from the memory means, a clock means for driving said channel select means, a display sync signal generator coupled to activate the channel select means and the memory address means in timed relation to activation of the display means, a register select means coupled to be driven from the channel select means and coupled to selectively activate said register means to sequence the output of the channels to said display means,
 a comparing means having a first input connected to said register means and a second input connected to a reference input source means to provide a selective comparison between the output of the register means and the reference means and thereby generate an output in accordance with the comparison therebetween, and logic means selectively connecting the comparing means to said channel color driver means to correspondingly activate one of the color driver means to thereby provide visual display of the related channel.

6. The apparatus of claim 5 including an adder means connected between the memory means and the register means, said adder means including a control input connected to the computer processing means for selective actuation of the adder means for shifting of selected channels.

7. The apparatus of claim 1 including a character generator means, a separate character memory means, means coupling the character memory means and the character generator means to the computer processing means to selectively transmit a character to said channels for character display.

8. The display apparatus of claim 7 including output combining means connected to said character generator means and to said controller means to receive data signals and connected to said color driver means whereby selected graphical display channels and character channels are presented in corresponding identifying color.

9. The apparatus of claim 1 including a character generator means having an internal sequencing means to produce an output related to a selected character for display in any one of said channels, said computing means including a shared character memory means, means connecting said character generator means to said shared character memory means for preselected presentation of characters in predetermined channels.

10. The apparatus of claim 9 wherein said computer processing means includes a memory demand means generating an anticipatory demand signal for selection of the graphical or character memory means, said controller having hold means operable to hold the graphical display means in an intermediate hold position, said memory demand means being coupled to the controller means and to the character generator means to selectively effectively decouple the graphical memory means to the computer means and to simultaneously activate said hold means and being coupled to defeat the operation of the character generator for a given channel.

11. The apparatus of claim 1 including shift means to shift the position of at least one of said channels.

12. In a multiple channel data color display apparatus having a television display means including a vertically oriented scan line and interrelated beam control means to generate vertically extended line segments for presentation of a plurality of monitored data in graphical form in a related plurality of presentation channels, a computing apparatus including a processing means for manipulation of data and memory means including a graphical shared memory means for storing of said line segment data for each channel means to monitor the data, a multiplexing means connecting the processing means to said graphical shared memory means, a line generator comparing means connected to said multiplexing means to receive the graphical shared memory means, a beam control means connected to the line generator comparing means including individual presettable color channel driver means for each channel, said line generator comparing means including a sequence controller for actuating said color driver means to present each channel on the television display means in accordance with a preselected color and the stored memory under the control of the computer processing means.

13. The apparatus of claim 12 wherein said line generator comparing means includes a plurality of pairs of registers for storing the beginning and end information for each of the line segments of each channel for each scan line, means connecting said registers to the graphical multiplexing means for sequential loading of the line segment information, a sequence controller including a channel selection means and a memory address means connected to the multiplexing means for sequential loading of the data regarding the line segments into said register means, a register select means driven from said channel select means and connected to the register means to selectively activate the pairs of registers, and a synchronizing signal generator connected to the channel select means and to the memory address means to sequentially and cyclically operate said sequence controller and the display means in synchronism.

14. The apparatus of claim 13 wherein said line generator comparing means further includes a digital comparator connected to the output of said register means and having a clock driven input means, and means connected to said synchronizing signal generator to activate, reset and drive said comparator to sequentially establish outputs related to the data information in said registers and thereby sequentially activate said channel driver means.

15. The color display apparatus of claim 12 wherein said color driver means include a plurality of presettable color driver circuits having dual adjustment means for individually and separately establishing preselected colors, logic means connected to said presettable color driver circuits and to the output of said comparator for energizing a corresponding color driver circuit for the preselected channel, said comparator establishing the position of the display of the color segment on the display means with said presettable color providing distinguishing characteristics between channels.

16. The color display apparatus of claim 12 wherein said display means includes means connected to the output of said comparator to shape the signal generating a line segment to thereby present an improved visual color graphical presentation in each channel.

17. The apparatus of claim 16 wherein said means emphasizes the initial turn-on of a line segment.

18. The display apparatus of claim 12 having a character generator, a character shared memory means, a character multiplexing means connecting the character shared memory means to the processing unit and to the character generator, means connecting the character generator to the beam control means.

19. The display apparatus of claim 18 wherein said character generator includes an integrated character generator circuit element adapted to establish predetermined output characters, and decoder means connected between the character generator means and the color driver means to selectively connect the output of the character generator including a coupling bus to the character generator multiplexing means, and a defeat means connected to said computer processing unit to terminate the operating of the character generator and reset the character generator to the next starting position.

20. The color display apparatus of claim 12 wherein said television display means includes multiple line interleaving.

21. The apparatus of claim 12 wherein said multiplexing means is biased to connect the shared memory to the display means, said computer processing means establishes a memory demand signal a predetermined time prior to actual demand, and said sequence controller including a hold means connected to receive said memory demand signal and responsive to complete a line segment sequence cycle and then establish a hold on the sequence controller.

22. In a multiple channel data color display apparatus having a television display means including vertically oriented even and odd scan lines, a plurality of different color drivers each of which produces a preselected color display, a computing apparatus including a processing means for manipulation of data and having a graphical shared memory means and a character shared memory means, means to monitor the data, an analog-to-digital conversion means coupled to the monitoring means and to the processing means, said processing means generate vertically extended line segment data for presentation of the monitored data in graphical form and to generate related alpha numerized presentations in separate channels, a graphical multiplexing means connecting the processing means to the graphical shared memory means, a character multiplexing means connecting the processing means to the character shared memory means, a character generator connected to the character shared memory means and to said color drivers to establish selected alpha numeric information channels, pairs of registers for storing the beginning and end information for each of the line segments of each of said channels, sequence controller connecting said registers to the multiplexing means for the graphical shared memory means for sequential loading of the line segment information into said registers, said sequence controller including a channel selection means and a memory address means connected to the graphical memory multiplexing means for sequential withdrawal of the data regarding the line segments, incrementing means for sequentially increasing of the address of the memory address means for sequential withdrawal of information from such memory, a register select means driven from said channel select means and connected to the registers to selectively activate the registers, a synchronizing signal generator connected to the channel select means and to the memory address means and to the address incrementing means to sequentially and to cyclically operate said sequence controller and the display means to operate the display means in synchronism with the sequence controller, a digital comparing means connected to the output of said pairs of registers and having a clock driven input means, means to activate said comparing means to establish a plurality of outputs related to the data information in said pairs of registers, logic means connecting said plurality of outputs to said color drivers for selectively establishing colors in accordance with preselected preset outputs, said comparing means establishing the position of the display of the line segments on the display means with said channel colors providing distinguishing characteristics from other channels.

23. The apparatus of claim 21 wherein said plurality of color drivers each include presettable color level controls for individually and separately establishing preselected colors, said display means including means connected to all of the outputs of said comparing means to emphasize the initial turn-on of each line segment to thereby present a continuous appearing color graphical presentation.

24. The apparatus of claim 22 wherein said character generator means includes an integrated character generator circuit element adapted to establish predetermined output characters, a decoder means connected between the character circuit element and the logic means to selectively connect the character generator output to said several channel drivers.

25. The apparatus of claim 23 wherein said computer processing means controlling said character memory means to introduce channel select coding means into said decoder means to select the color channel.

26. The apparatus of claim 22 wherein said computer processing means includes a memory demand signal means a predetermined time before actual coupling to the memory means,
said demand signal means being connected to activate such sequence controller to complete a readout sequence for a given line segment and then to remain in stand-by position until the computer completes its processing to the shared memory.

27. The apparatus of claim 26 wherein said demand signal means of said computer processing means is connected to the character generator to terminate and reset the character generator.

28. The color display apparatus of claim 2 including a binary adder connected between the register means and the graphical shared memory means, said adder having an input means connected to the computer processing means and selectively actuated to shift the presentation of said channels.

* * * * *

UNITED STATES PATENT AND TRADEMARK OFFICE
CERTIFICATE OF CORRECTION

PATENT NO. : 3,978,470
DATED : August 31, 1976
INVENTOR(S) : LAURENCE T. McGUIRE It is certified that error appears in the above-identified patent and that said Letters Patent are hereby corrected as shown below:

Column 1, Line 61, cancel "defintion" and insert --- definition ---; and after "of" insert --- a ---;

Column 6, Line 51, after "and" cancel "the";

Column 16, Line 20, after "claim" cancel "2" and insert --- 22 ---.

Signed and Sealed this

Twenty-eighth Day of December 1976

[SEAL]

Attest:

RUTH C. MASON
*Attesting Officer*

C. MARSHALL DANN
*Commissioner of Patents and Trademarks*